United States Patent
Kapadia

(10) Patent No.: US 10,660,718 B2
(45) Date of Patent: May 26, 2020

(54) SURGICAL ASSEMBLIES FOR HOUSING FORCE TRANSMITTING MEMBERS

(71) Applicant: Covidien LP, Mansfield, MA (US)

(72) Inventor: Jaimeen Kapadia, Bridgeport, CT (US)

(73) Assignee: COVIDIEN LP, Mansfield, MA (US)

( * ) Notice: Subject to any disclaimer, the term of this patent is extended or adjusted under 35 U.S.C. 154(b) by 561 days.

(21) Appl. No.: 15/306,705

(22) PCT Filed: Apr. 1, 2015

(86) PCT No.: PCT/US2015/023787
§ 371 (c)(1),
(2) Date: Oct. 25, 2016

(87) PCT Pub. No.: WO2015/167740
PCT Pub. Date: Nov. 5, 2015

(65) Prior Publication Data
US 2017/0049522 A1    Feb. 23, 2017

Related U.S. Application Data

(60) Provisional application No. 61/985,024, filed on Apr. 28, 2014.

(51) Int. Cl.
*A61B 34/00*         (2016.01)
*A61B 34/30*         (2016.01)
(Continued)

(52) U.S. Cl.
CPC .......... *A61B 34/71* (2016.02); *A61B 1/00101* (2013.01); *A61B 34/30* (2016.02);
(Continued)

(58) Field of Classification Search
CPC .... A61B 2017/2901; A61B 2017/2902; A61B 2017/2912; A61B 10/06; A61B 17/29;
(Continued)

(56) References Cited

U.S. PATENT DOCUMENTS

| | | | | |
|---|---|---|---|---|
| 5,441,494 A | * | 8/1995 | Ortiz | ......................... B25J 3/00 |
| | | | | 294/213 |
| 5,716,352 A | * | 2/1998 | Viola | ............... A61B 17/00234 |
| | | | | 128/898 |

(Continued)

FOREIGN PATENT DOCUMENTS

| CN | 101516273 A | 8/2009 |
|---|---|---|
| DE | 2820239 A1 | 11/1978 |

(Continued)

OTHER PUBLICATIONS

VectorStock: Keyhole key icons Vintage keys and keyholes signs cevtor image as accessed Apr. 24, 2019; https://www.vectorstock.com/royalty-free-vector/keyhole-key-icons-vintage-keys-and-keyholes-signs-vector-10571114.*

(Continued)

*Primary Examiner* — Wade Miles

(57) ABSTRACT

An endoscopic surgical assembly houses at least one force transmitting member that is connected to a surgical attachment supported on the endoscopic surgical assembly. The endoscopic surgical assembly includes an elongate shaft having a proximal end and a distal end configured for connection to a surgical attachment. At least one longitudinal cavity is formed in an outer surface of the elongate shaft and extends between the proximal and distal ends of the elongate shaft. The at least one longitudinal cavity is configured for disposal of the at least one force transmitting member therein such that the at least one force transmitting member is translatable relative to the elongate shaft.

7 Claims, 5 Drawing Sheets

(51) Int. Cl.
  *A61B 17/29* (2006.01)
  *A61B 90/00* (2016.01)
  *A61B 1/00* (2006.01)
(52) U.S. Cl.
  CPC ...... *A61B 90/08* (2016.02); *A61B 2017/2901* (2013.01); *A61B 2017/2936* (2013.01); *A61B 2034/305* (2016.02); *A61B 2090/0813* (2016.02)
(58) Field of Classification Search
  CPC ........... A61B 2017/00318; A61B 2017/00323; A61B 2017/00327; A61B 17/32053; A61M 25/1033; A61M 25/0147; A61M 2025/015; A61M 25/09041; B25J 13/02; B25J 3/00
  See application file for complete search history.

(56) References Cited

U.S. PATENT DOCUMENTS

| | | | |
|---|---|---|---|
| 5,749,879 A * | 5/1998 | Middleman | A61B 10/02 606/139 |
| 6,371,952 B1 * | 4/2002 | Madhani | A61B 17/00234 606/1 |
| 7,648,519 B2 | 1/2010 | Lee et al. | |
| 7,854,738 B2 * | 12/2010 | Lee | A61B 34/20 606/130 |
| 7,918,783 B2 | 4/2011 | Maseda et al. | |
| 8,088,062 B2 | 1/2012 | Zwolinski | |
| 8,915,940 B2 * | 12/2014 | Steege | A61B 17/29 606/205 |
| 8,992,422 B2 * | 3/2015 | Spivey | A61B 34/30 600/153 |
| 10,004,498 B2 * | 6/2018 | Morgan | A61B 17/072 |
| 2002/0072766 A1 * | 6/2002 | Hunt | A61B 17/29 606/205 |
| 2002/0096177 A1 * | 7/2002 | Toti | A61M 16/04 128/207.15 |
| 2003/0135204 A1 | 7/2003 | Lee et al. | |
| 2004/0193146 A1 * | 9/2004 | Lee | A61B 17/062 606/1 |
| 2004/0236316 A1 * | 11/2004 | Danitz | A61B 1/0055 606/1 |
| 2007/0208375 A1 * | 9/2007 | Nishizawa | A61B 17/29 606/205 |
| 2008/0065116 A1 | 3/2008 | Lee et al. | |
| 2010/0160929 A1 | 6/2010 | Rogers et al. | |
| 2010/0198253 A1 * | 8/2010 | Jinno | A61B 17/29 606/205 |
| 2010/0249818 A1 * | 9/2010 | Jinno | A61B 17/29 606/174 |
| 2011/0022078 A1 * | 1/2011 | Hinman | A61B 17/29 606/206 |
| 2011/0163146 A1 | 7/2011 | Ortiz et al. | |
| 2011/0172648 A1 * | 7/2011 | Jeong | A61B 17/29 606/1 |
| 2011/0277776 A1 | 11/2011 | McGrogan et al. | |
| 2012/0116416 A1 | 5/2012 | Neff et al. | |
| 2013/0030462 A1 * | 1/2013 | Keating | A61B 17/0218 606/206 |
| 2013/0140835 A1 * | 6/2013 | Stefanchik | A61B 17/29 294/106 |
| 2014/0350570 A1 * | 11/2014 | Lee | A61B 17/2909 606/130 |
| 2015/0150635 A1 * | 6/2015 | Kilroy | B25J 15/0028 606/130 |

FOREIGN PATENT DOCUMENTS

| | | |
|---|---|---|
| DE | 10034105 C1 | 4/2002 |
| EP | 3125813 A1 | 2/2017 |
| JP | 53139390 | 12/1978 |
| JP | 2006180933 A | 7/2006 |
| JP | 2007252922 A | 10/2007 |
| JP | 2009-220219 | 10/2009 |

OTHER PUBLICATIONS

Merriam-Webster definition for "cam" as accessed Aug. 21, 2019; https://www.merriam-webster.com/dictionary/cam.*
Chinese First Office Action corresponding to counterpart Patent Appln. CN 201580022774.7 dated Jul. 3, 2018.
Japanese Office Action corresponding to counterpart Patent Application JP 2016-564997 dated Jan. 28, 2019.
Extended European Search Report corresponding to counterpart Int'l Appln. No. EP 15 78 5333.4 dated Nov. 29, 2017.
International Search Report for (PCT/US2015/023787) date of completion is Jun. 16, 2015 (4 pages).

* cited by examiner

SURGICAL ASSEMBLIES FOR HOUSING FORCE TRANSMITTING MEMBERS

CROSS-REFERENCE TO RELATED APPLICATIONS

This application is a U.S. National Stage Application filed under 35 U.S.C. § 371(a) of International Patent Application Serial No. PCT/US2015/023787, filed Apr. 1, 2015, which claims the benefit of U.S. Provisional Patent Application Ser. No. 61/985,024, filed Apr. 28, 2014, the entire disclosure of each of which is incorporated by reference herein.

BACKGROUND

Robotic surgical systems have been used in minimally invasive medical procedures. Some robotic surgical systems included a console supporting a robot arm, and at least one end effector such as forceps or a grasping tool that is mounted to the robot arm via a surgical assembly or tool. The end effector was typically affixed to the end of a longitudinal shaft of the tool. During a medical procedure, the longitudinal shaft and the end effector were inserted into a small incision (via a cannula) or a natural orifice of a patient to position the end effector at a work site within a body of a patient.

This shaft had a hollow tube carrying the cables therethrough. The cables were connected to the end effector at the end of the shaft and driven by motors in the robotic system to manipulate the end effector. Bodily fluids tended to flow into the hollow interior of the tube during surgery. These fluids had to be cleaned out prior to use in another surgical procedure. Cleaning and/or sterilizing the hollow interior of the tube was difficult and time-consuming. Indeed, it was not uncommon to find tissue and/or blood remaining within the tube even after an attempt was made to clean and/or sterilize it. Further, routing the cables through the lengthy interior of the tube was time consuming.

Accordingly, there is a need to manipulate end effectors using cables or other force transmitting members in way that it is easier to clean, sterilize, assemble, and service the surgical tools.

SUMMARY

Surgical tools may be made easier to clean, sterilize, assemble, and service by forming at least one lengthwise opening in an outer surface of a shaft where a force transmitting member, such as a cable, may be inserted. The lengthwise opening may extending from one end of the shaft to the other and may be sized to enable the force transmitting member to move up and down longitudinally along the length of the shaft once the member is inserted in the opening. Once the force transmitting member has been inserted in the opening, a sleeve may be placed over the outer surface of the shaft to cover the opening in the outer surface of the shaft. The sleeve may also be used to contain the force transmitting member within the opening in the shaft.

Once a surgical procedure has been completed, the sleeve may be separated from the shaft and the force transmitting member may be removed from the opening. A cleaning substance may be directly applied to the opening walls along the length of the opening in the shaft, instead of just the ends of the shaft as was done in the past. This may enable a more thorough cleaning of the shaft and the force transmitting member.

Providing the lengthwise opening along the shaft length enables a quicker assembly of the surgical tool as there is no longer a need to feed cables through the length of a hollow shaft from a single opening at one end of the shaft. Additionally, as discussed previously, the lengthwise opening enables more cleaning substances to be directly applied to the walls of the opening where blood and other contaminants collect during the surgical procedure resulting in a more thorough cleaning of the tool.

In some instances, jaws may be coupled to an end of the shaft and attached to different force transfer members inserted in different shaft openings. The jaws may include forceps or scissor cutting tools that are part of a cable/tube and gear system that may also include two or more force transfer members, a shaft with two or more longitudinal surface openings housing each respective force transfer member, and a sleeve covering the shaft so as to cover the surface openings and contain each force transfer member in its respective opening. In some instances, the cable/tube and gear system may be driven directly so at least one cable/tube controls a pitch, at least one cable/tube controls a jaw, and at least one cable/tube opens and closes the jaws.

End effectors, including wrist assemblies and jaw assemblies, may be used with and actuated by robotic surgical systems. In some instances, an end effector may be controlled and/or articulated by at least one cable/tube extending from a respective motor of a control device of the robot surgical system, through a cable carrying member and to a surgical attachment, such as, for example, an end effector.

According to one aspect of the present disclosure, an endoscopic surgical assembly is provided. The endoscopic surgical assembly houses at least one force transmitting member that is connected to a surgical attachment supported on the endoscopic surgical assembly. The endoscopic surgical assembly includes an elongate shaft having a proximal end and a distal end. The distal end is configured for connection to a surgical attachment. At least one longitudinal cavity is formed in an outer surface of the elongate shaft. The at least one longitudinal cavity extends between the proximal and distal ends of the elongate shaft. The at least one longitudinal cavity is configured for disposal of the at least one force transmitting member therein such that the at least one force transmitting member is translatable relative to the elongate shaft.

In some instances, the at least one longitudinal cavity may have a key-hole shaped transverse cross-sectional profile though in other instances the cavity may have a different cross-sectional profile. In some embodiments, the at least one longitudinal cavity may have a diameter substantially equal to a diameter of the at least one force transmitting member.

It is contemplated that the endoscopic surgical assembly may further include a sleeve disposable about the elongate shaft to sheath the at least one force transmitting member within the at least one longitudinal cavity. In some embodiments, the sleeve may retain the at least one force transmitting member between the outer surface of the elongate shaft and the sleeve.

It is envisioned that the elongate shaft may have a cylindrical configuration.

In some embodiments, the at least one longitudinal cavity may include a plurality of longitudinal cavities disposed in parallel alignment circumferentially about the elongate shaft. A force transmitting member may be slidably disposed within each longitudinal cavity.

In accordance with another aspect of the present disclosure, an electromechanical surgical system is provided. The surgical system includes an endoscopic surgical assembly configured to support a surgical attachment. The surgical attachment is configured to perform at least one function. The endoscopic surgical assembly comprises an elongate shaft extending between and having a proximal end and a distal end. The distal end is configured for selective connection of the surgical attachment thereto. The elongate shaft defines a plurality of longitudinal cavities formed in an outer surface thereof. The longitudinal cavities extend between the proximal and distal ends of the elongate shaft. A plurality of force transmitting members are connected to the surgical attachment. A member of the plurality of force transmitting members is translatably disposed in each longitudinal cavity.

In aspects of the present disclosure, each of the plurality of longitudinal cavities may have a key-hole, U-shaped, V-shaped, or other shaped transverse cross-sectional profile. In some embodiments, each of the plurality of longitudinal cavities may have a diameter substantially equal to a diameter of each of the plurality of force transmitting members.

The electromechanical surgical system may further include a sleeve disposable about the elongate shaft to sheath each of the plurality of force transmitting members within a respective one of the plurality of longitudinal cavities. The sleeve may also retain each of the plurality of force transmitting members between the outer surface of the elongate shaft and the sleeve.

It is contemplated that the elongate shaft may have a cylindrical configuration.

It is envisioned that the plurality of longitudinal cavities may be disposed in parallel alignment circumferentially about the elongate shaft.

In accordance with yet another aspect of the present disclosure, a method of preparing an electromechanical surgical system is provided. The method includes providing an endoscopic surgical assembly supporting a surgical attachment. The surgical attachment is configured to perform at least one function. The endoscopic surgical assembly includes an elongate shaft extending between and having a proximal end and a distal end. The distal end is configured for selective connection of the surgical attachment thereto. The elongate shaft defines a plurality of longitudinal cavities formed in an outer surface thereof. The longitudinal cavities extend between the proximal and distal ends of the elongate shaft. The method further includes providing a plurality of force transmitting members connected to the surgical attachment. A force transmitting member is translatably disposed in each longitudinal cavity. The method further includes disposing a first sleeve about the elongate shaft to enclose each of the plurality of force transmitting members within a respective one of the plurality of longitudinal cavities. The sleeve also disposes each of the plurality of force transmitting members between the outer surface of the elongate shaft and the sleeve.

In aspects of the present disclosure, the method may further include removing the first sleeve from the elongate shaft; cleaning the elongate shaft and the plurality of force transmitting members; and disposing a second sleeve about the elongate shaft. In some embodiments, cleaning the elongate shaft may include at least one of autoclaving, steaming, chemical cleaning, and drying the plurality of longitudinal cavities.

In embodiments, the method may further include removing the first sleeve from the elongate shaft; and disposing a second sleeve about the elongate shaft.

It is contemplated that the method may further include at least one of: cleaning the elongate shaft and the plurality of force transmitting members; and replacing the plurality of force transmitting members.

It is envisioned that disposing the first sleeve about the elongate shaft may include sliding the first sleeve over the surgical attachment and onto the elongate shaft.

In aspects of the present disclosure, the method may further include shrink-wrapping the first sleeve onto the elongate shaft.

The method may further comprise replacing the plurality of force transmitting members.

Further details and aspects of exemplary embodiments of the present disclosure are described in more detail below with reference to the appended figures.

As used in the present disclosure, the terms parallel and perpendicular are understood to include relative configurations that are substantially parallel and substantially perpendicular up to about +/−10 degrees from true parallel and true perpendicular.

BRIEF DESCRIPTION OF THE DRAWINGS

Embodiments of the present disclosure will now be described with reference to the accompanying drawings, wherein.

DETAILED DESCRIPTION

Figure 1A:
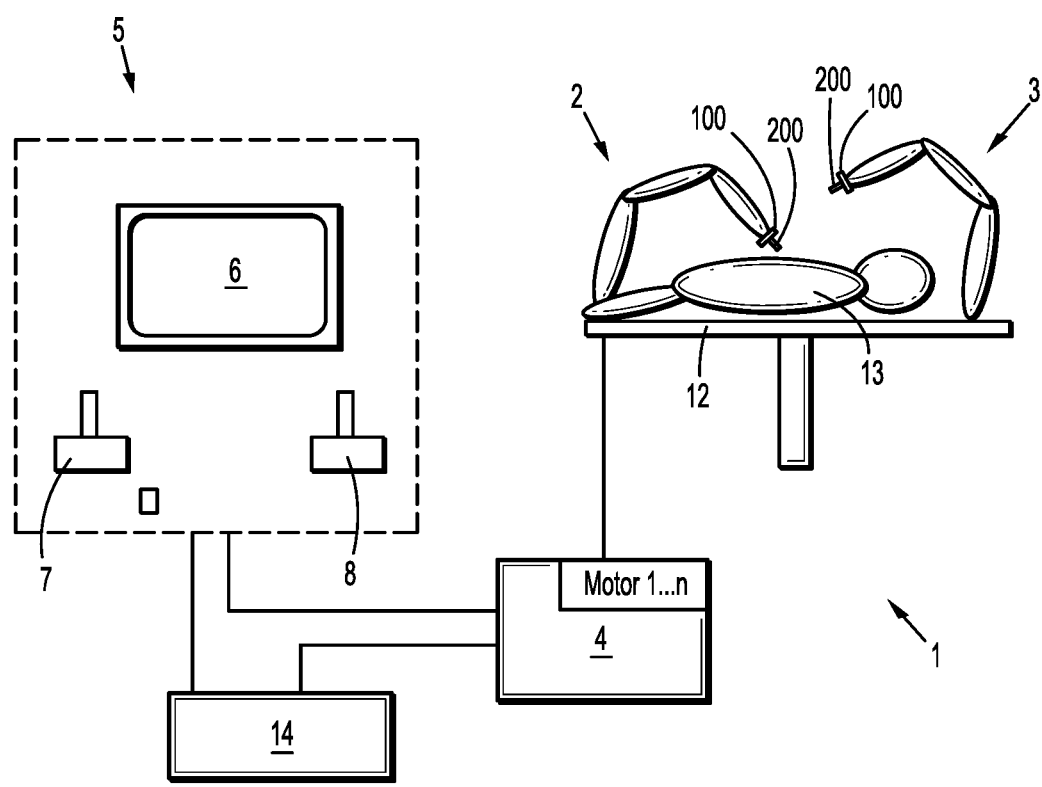
FIG. 1A is a schematic illustration of one illustrative embodiment of an electromechanical surgical system and operating console in accordance with the present disclosure.

Embodiments of the presently disclosed surgical assembly, such as, for example, an endoscopic surgical assembly, are described in detail with reference to the drawings, in which like reference numerals designate identical or corresponding elements in each of the several views. As used herein the term "distal" refers to that portion of the endoscopic surgical assembly that is farther from the user, while the term "proximal" refers to that portion of the endoscopic surgical assembly that is closer to the user.

Referring initially to FIG. 1A, a medical work station or electromechanical surgical system is shown generally as surgical system 1 and generally includes a plurality of robot arms 2, 3; a control device 4; and an operating console 5 coupled with control device 4. Operating console 5 includes a display device 6, which is set up in particular to display three-dimensional images; and manual input devices 7, 8, by means of which a person (not shown), for example a surgeon, is able to telemanipulate robot arms 2, 3 in a first operating mode, as known in principle to a person skilled in the art.

Each of the robot arms 2, 3 includes a plurality of members, which are connected through joints, and a surgical assembly 100 to which may be attached, for example, a surgical attachment, such as, for example, an end effector 200, in accordance with any one of several embodiments disclosed herein, as will be described in greater detail below. A distal end of surgical assembly 100 is configured to support a plurality of different end effectors, including, but not limited to a surgical stapler, a surgical cutter, a surgical stapler-cutter, a linear surgical stapler, a linear surgical stapler-cutter, a circular surgical stapler, a circular surgical stapler-cutter, a surgical clip applier, a surgical clip ligator, a surgical clamping device, a vessel expanding device, a lumen expanding device, a scalpel, a fluid delivery device or any other type of surgical instrument, each of which being configured for actuation and manipulation by the robot arms 2, 3 via force transmitting members, such as, for example, cables "C," as described below. In embodiments, the force transmitting members can be variously configured, such as, for example, hypotubes, push rods, shafts, or tethers, and can transmit various forces, such as, for example, axial (i.e., pushing and pulling), rotary, and/or torque.

Robot arms 2, 3 may be driven by electric drives that are connected to control device 4. Control device 4 (e.g., a computer) is set up to activate the drives, in particular by means of a computer program, in such a way that robot arms 2, 3, their surgical assemblies 100 and thus the end effector 200 execute a desired movement according to a movement defined by means of manual input devices 7, 8. Control device 4 may also be set up in such a way that it regulates the movement of robot arms 2, 3 and/or of the drives.

Surgical system 1 is configured for use on a patient 13 lying on a patient table 12 to be treated in a minimally invasive manner by means of end effector 200. Surgical system 1 may also include more than two robot arms 2, 3, the additional robot arms likewise being connected to control device 4 and being telemanipulatable by means of operating console 5. A surgical attachment or end effector 200 may also be attached to the additional robot arm. Surgical system 1 may include a database 14 coupled with control device 4, in which are stored, for example, preoperative data from patient 13 and/or anatomical atlases.

For a detailed description of the construction and operation of surgical system 1, reference may be made to U.S. Patent Publication No. 2012/0116416, filed on Nov. 3, 2011, entitled "Medical Workstation," the entire content of which is incorporated herein by reference.

Figure 1B:
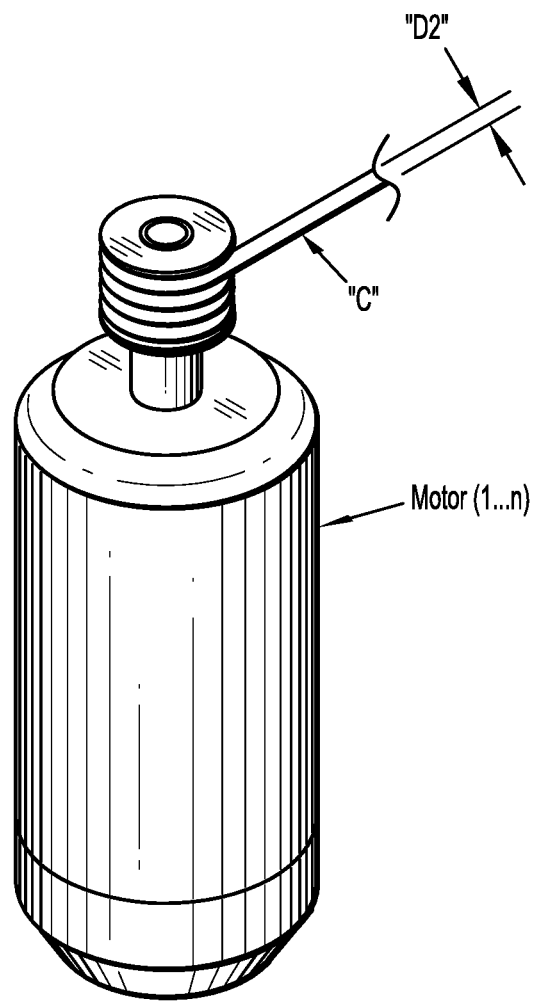
FIG. 1B is a schematic, perspective view of a motor of a control device of the surgical system of FIG. 1A connected with a force transmitting force transmitting member.

Control device 4 may control a plurality of motors (Motor 1 . . . n) with each motor configured to wind-up or let out a length of a force transmitting cable(s) "C" (FIG. 1B) extending through each robot arm 2, 3, surgical assembly 100 and to end effector 200, or to rotate a gear or a drive shaft (not shown). In use, as cables "C" are wound-up and let out, cables "C", gears or drive shafts may effect operation and/or movement of each end effector 200 of surgical assembly 100. It is contemplated that control device 4 coordinates the activation of the various motors (Motor 1 . . . n) to coordinate a winding-up or letting out a length of a respective cable "C" in order to coordinate an operation and/or movement of a respective end effector 200. Although FIG. 1B shows a single cable "C" that is wound up or let out by a single motor, in some instances a plurality of cables or two ends of a single cable may be wound up or let out by a single motor. For example, in some instances, two cables or cable ends may be coupled in opposite directions to a single motor so that as the motor is activated in a first direction, one of the cables winds up while the other cable lets out. Other cable configurations may be used in different embodiments. It is contemplated that a plurality of cables are each engaged to a respective motor of a plurality of motors.

Figure 4:
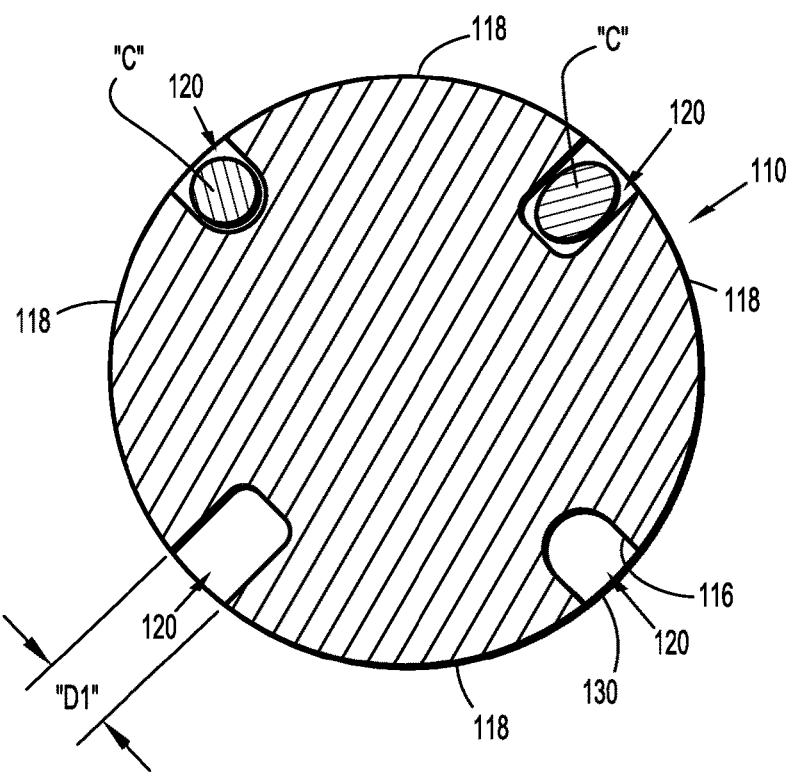
FIG. 4 is cross-sectional view of the elongate shaft taken along section line 4-4 of FIG. 3.
Figure 5:
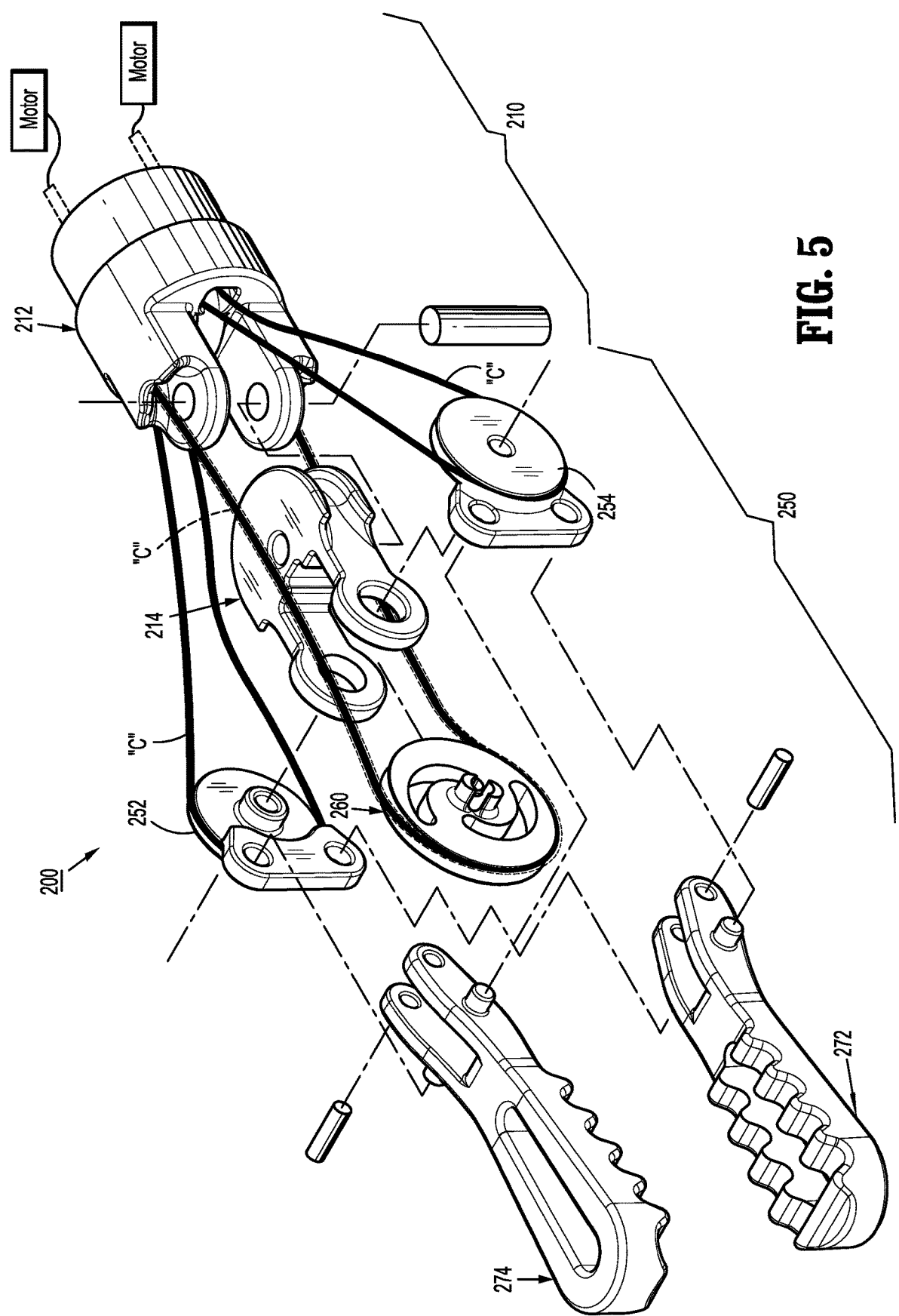
FIG. 5 is a partial perspective view, with parts separated, of a surgical attachment for use with the surgical assembly shown in FIG. 1A.

Turning to FIGS. 2-5, illustrated is a surgical tool or endoscopic surgical assembly 100 configured for interconnection between a robot arm, such as, for example, one of robot arms 2 or 3 shown in FIG. 1A and an end effector 200 shown in FIG. 5. Surgical assembly 100 houses at least one force transmitting cable "C" that is connected to end effector 200 supported on surgical assembly 100. Surgical assembly 100 includes a body portion 102 connected to robot arms 2 or 3; and an elongate shaft 110 extending from body portion 102.

Elongate shaft 110 has a proximal end 112 and a distal end 114 defining a central longitudinal axis "X1-X1" therebetween. Distal end 114 is configured for selective connection of end effector 200 thereto, which performs various surgical functions via actuation of force transmitting cables "C." In embodiments, proximal end 112 of elongate shaft 110 is rotatably disposed with body portion 102. It is contemplated that proximal end 112 of elongate shaft 110 is integrally and/or monolithically formed with body portion 102.

Elongate shaft 110 has a cylindrical configuration and may be cannulated or non-cannulated. In embodiments, elongate shaft 110 may be variously configured, such as, for example, rectangular, oval, oblong, hexagonal, tapered, undulating, triangular, square, polygonal, irregular, uniform, non-uniform and/or variable. As used herein, the term "non-cannulated" is understood to relate to elongate shaft 110 having a solid, substantially non-porous, monolithic core not having a passageway extending through central longitudinal axis "X1-X1" thereof. Further, as shown in FIG. 4, elongate shaft 110 has a substantial absence of cavities other than longitudinal cavities or channels 120 formed in its outer surface 116, as described below. In some embodiments, elongate shaft 110 may be cannulated, i.e., elongate shaft 110 may include a longitudinal passageway extending therethrough.

Elongate shaft 110 can be fabricated from various materials, such as, for example, carbon fiber, plastic, nylon, stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol), ceramics and composites thereof such as calcium phosphate, thermoplastics such as polyaryletherketone (PAEK) including polyetheretherketone (PEEK), polyetherketoneketone (PEKK) and polyetherketone (PEK), carbon-PEEK composites, polyethylene terephthalate (PET), silicone, polyurethane, silicone-polyurethane copolymers, semi-rigid and rigid materials.

Elongate shaft 110 may have material composites, including the above materials, to achieve various desired characteristics such as strength, rigidity, elasticity, compliance, and durability. Elongate shaft 110 may also be fabricated from a heterogeneous material such as a combination of two or more of the above-described materials.

Elongate shaft 110 has an outer surface 116. Outer surface 116 is smooth and substantially non-porous to resist absorption and/or adherence of bodily fluids during a surgical procedure. Outer surface 116 has a plurality of arcuate segments 118 extending between proximal and distal ends 112, 114 of elongate shaft 110.

At least one longitudinal cavity or channel 120 is formed in outer surface 116 of elongate shaft 110 and disposed between arcuate segments 118. Longitudinal cavities or channels 120 extend between proximal and distal ends 112, 114 of elongate shaft 110. Channels 120 are each configured for disposal of a force transmitting cable "C" therein such that cables "C" are translatable relative to elongate shaft 110 and within longitudinal cavities or channels 120. Channels 120 are disposed in parallel alignment circumferentially about elongate shaft 110, such that a cross section of outer surface 116 of elongate shaft 110 includes an alternating pattern of arcuate segments 118 and channels 120, as shown in FIG. 4. Channels 120 may run parallel with central longitudinal axis "X1-X1" of elongate shaft 110 in a straight-lined configuration. In some embodiments, channels 120 may spiral about central axis "X1-X1", in a helical manner, between proximal and distal ends 112, 114 of elongate shaft 110.

Channels 120 each have a U-shaped transverse cross-sectional profile. In some instances, the cross-sectional profile may be key hole shaped or otherwise configured to correspond to an arcuate outer surface of force transmitting cables "C" so as to facilitate retention of cables "C" within channels 120 and a sliding or translation of cables "C" within channels 120. In embodiments, channels 120 may have cross-sectional configurations such as, for example, U-shaped, arcuate, square, rectangular, oval, oblong, V-shaped, polygonal, triangular, tapered, non-uniform, uniform and/or variable. Channels 120 each have a diameter "D1" substantially equal to a diameter "D2" of cables "C." In this way, cables "C," upon insertion into respective longitudinal cavities or channels 120, fit securely and translatably therein.

Figure 2:
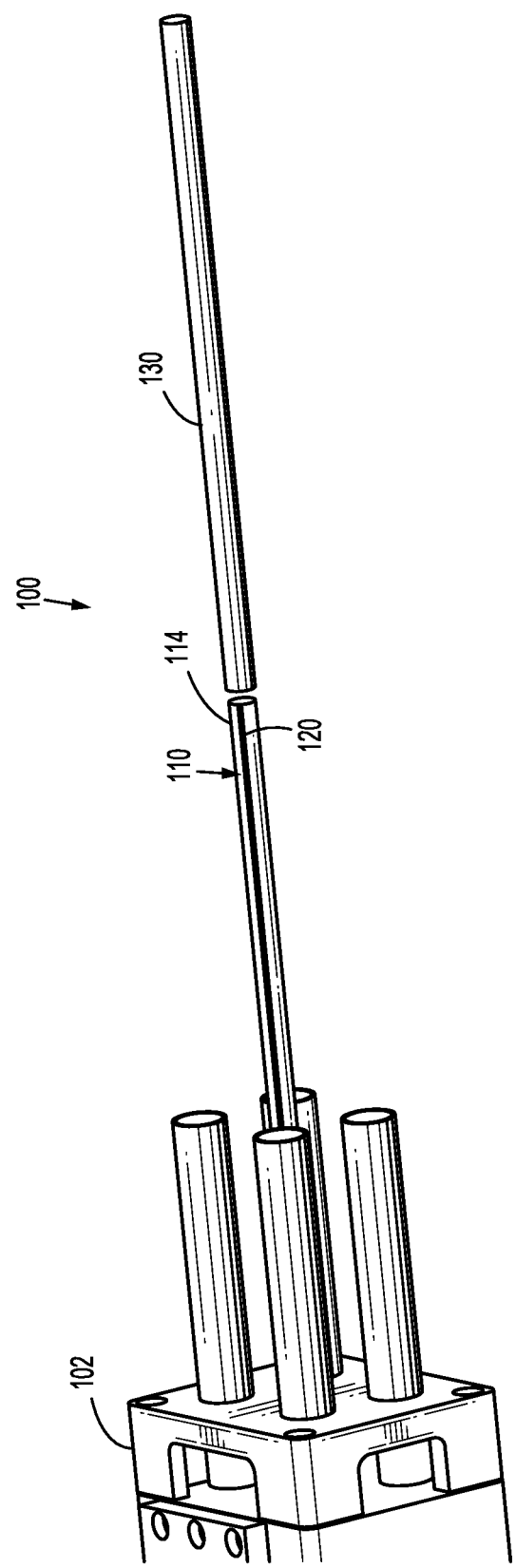
FIG. 2 is a perspective view, with some parts separated, of a surgical assembly, according to an embodiment of the present disclosure, of the surgical system shown in FIG. 1A.
Figure 3:
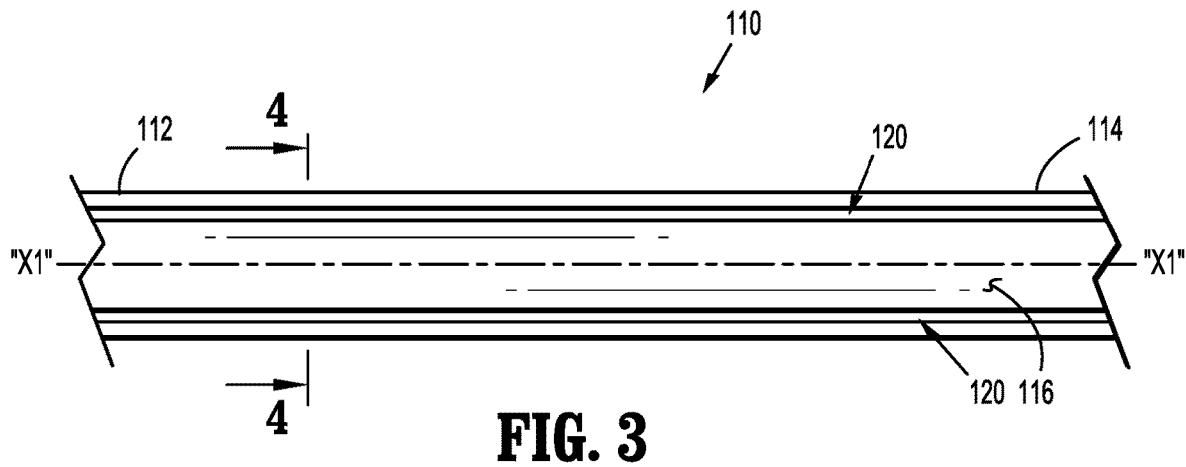
FIG. 3 is a side view of an elongate shaft of the surgical assembly shown in FIG. 2.

With reference to FIGS. 2 and 4, surgical assembly 100 further includes a sleeve 130 disposable about elongate shaft 110 to sheath cables "C" within respective channels 120. Sleeve 130 also retains cables "C" between outer surface 116 of elongate shaft 110 and sleeve 130. Sleeve 130 is sized and dimensioned to slide over elongate shaft 110 while cables "C" are retained within channels 120. Sleeve 130 is fabricated from a substantially non-porous material so as to resist and/or prevent the passing of bodily fluids, such as, for example, blood and tissue from a surgical site through sleeve 130 and into channels 120. Sleeve 130 may be fabricated from plastic or any other suitable material that would provide for smooth movement through a trocar and a good seal.

As shown in FIG. 5, surgical assembly 100 further includes a surgical attachment, such as, for example, an end effector 200, which is configured for operative connection with distal end 114 of elongate shaft 110 of surgical assembly 100 and for manipulation by control device 4. Force transmitting cables "C" are connected to end effector 200 and are configured to actuate the various functions performed by end effector 200 by sliding or translating within channels 120 relative to elongate shaft 110.

In the illustrated embodiment, end effector 200 includes a wrist assembly 210, and a jaw assembly 250 pivotally connected to wrist assembly 210. Wrist assembly 210 includes a proximal hub 212, in the form of a distally extending clevis. Wrist assembly 210 further includes a distal hub 214 pivotally connected to proximal hub 212. Distal hub 214 may be in the form of a distally extending clevis. End effector 200 includes a jaw assembly 250 having a pair of spaced apart support or cam plates, or cam pulleys 252, 254 pivotally connected to distal hub 214 of wrist assembly 210.

A single first cable "C" is at least partially wrapped around cam pulley 252 and secured to at least one point thereof, or that the single first cable "C" may be wrapped at least once around cam pulley 252, in the manner of a capstan. Single first cable "C" may include proximal ends that extend through one of channels 120 and robot arm 2 or 3 and operatively associated with a respective first motor and second motor (Motor 1 . . . n) of control device 4. While a single first cable "C" is shown and described, it is contemplated that a first pair of cables (not shown) including respective distal ends may be secured to opposed sides of cam pulley 252, or wrapped at least 180° around cam pulley 252 and secured thereto, and including respective proximal ends extending through one of longitudinal cavities or channels 120 of elongate shaft 110 and robot arm 2 or 3 and operatively associated with a respective first motor and second motor (Motor 1 . . . n) of control device 4.

A single second cable "C" is at least partially wrapped around cam pulley 254 and secured to at least one point thereof, or that the single second cable "C" may be wrapped at least once around cam pulley 254, in the manner of a capstan. Single second cable "C" may include proximal ends that extend through one of channels 120 of elongate shaft 110 and robot arm 2 or 3 and operatively associated with a respective first motor and second motor (Motor 1 . . . n) of control device 4. While a single second cable "C" is shown and described, it is contemplated that a first pair of cables (not shown) including respective distal ends may be secured to opposed sides of cam pulley 254, or wrapped at least 180° around cam pulley 254 and secured thereto, and including respective proximal ends extending through one of longitudinal cavities or channels 120 of elongate shaft 110 and robot arm 2 or 3 and operatively associated with a respective first motor and second motor (Motor 1 . . . n) of control device 4.

Jaw assembly 250 further includes a cam pulley 260 also pivotally connected to distal hub 214 of wrist assembly 210. Jaw assembly 250 also includes a pair of jaws 272, 274 separately and independently pivotally connected to support pulleys 252, 254. Specifically, each jaw 272, 274 includes a pivot point about which each jaw 272, 274 pivots. Jaws 272, 274 are pivotally and slidably connected to cam pulley 260. In use, as cam pulley 260 is rotated in either a clockwise or counter clockwise direction, jaws 272, 274 will be caused to be opened or closed accordingly. Each of jaws 272, 274 defines a grip or toothed portion in juxtaposed relation to one another.

A single third cable "C" is at least partially wrapped around cam pulley 260 and secured to at least one point thereof, or that the single third cable "C" may be wrapped at least once around cam pulley 260, in the manner of a capstan. Single third cable "C" extends through one of channels 120 of elongate shaft 110 and robot arm 2 or 3 and operatively associated with a respective fifth motor (Motor 1 . . . n) and sixth motor (Motor 1 . . . n) of control device 4. While a single third cable "C" is shown and described, it is contemplated that a third pair of cables (not shown) including respective distal ends may be secured to opposed sides of cam pulley 160, or wrapped at least 180° around cam pulley 160 and secured thereto, and including respective proximal ends extending through one of channels 120 of elongate shaft 110 and robot arm 2 or 3 and operatively associated with a respective fifth motor (Motor 1 . . . n) and sixth motor (Motor 1 . . . n) of control device 4.

For a detailed description of the construction and operation of end effector 200, as illustrated in FIG. 5, reference may be made to U.S. Provisional Patent Application Ser. No. 61/914,632, filed on Dec. 11, 2013, entitled "WRIST AND JAW ASSEMBLIES FOR ROBOTIC SURGICAL SYSTEMS".

In operation, body portion 102 of surgical assembly 100 is engaged with a distal end of robot arms 2 or 3. Force transmitting cables "C" are inserted into respective channels 120. Sleeve 130 is disposed about elongate shaft 110 to enclose each cable "C" within a respective one of channels 120. Sleeve 130 is disposed about elongate shaft 110 by sliding sleeve 130 over end effector 200 and onto elongate shaft 110. In some embodiments, with sleeve 130 disposed about elongate shaft 110, sleeve 130 is shrink-wrapped onto elongate shaft 110 to dispose each of cables "C" between outer surface 116 of elongate shaft 110 and sleeve 130. Alternatively, a sheet of material may be wrapped about elongate shaft 110 and adhered to itself to form a sleeve.

After a particular surgical procedure is performed and surgical assembly 100 is withdrawn from a surgical site of patient 13, sleeve 130 is removed from elongate shaft 110, exposing cables "C" and outer surface 116 of elongate shaft 110 to allow for easier access to surfaces of elongate shaft 110 needing cleaning. Cables "C" are disengaged from or slid out of channels 120. Outer surface 116 and channels 120 of elongate shaft 110 are cleaned to remove any debris accumulated during the surgical procedure. Elongate shaft 110 is cleaned by autoclaving, steaming, chemical cleaning and/or drying. Cables "C" can also be cleaned, e.g., by the same methods used to clean elongate shaft 110, described above. Alternatively, cables "C" can be replaced with new replacement cables not previously used during the surgical procedure. In some embodiments, cables "C" are not removed prior to cleaning.

With either cables "C" or replacement cables (not shown) disposed in channels 120, a replacement sleeve (not shown), similar to sleeve 130 described above, not previously used during the surgical procedure, can be slid over end effector 200 and onto elongate shaft 110. It is contemplated that sleeve 130 can be discarded, or cleaned and reused. Surgical assembly 100 is then ready to be used for another surgical procedure.

It will be understood that various modifications may be made to the presently disclosed embodiments. Therefore, the above description should not be construed as limiting, but merely as exemplifications of various embodiments. Those skilled in the art will envision other modifications within the scope and spirit of the claims appended thereto.

What is claimed is:

1. An endoscopic surgical assembly comprising:
    an elongate shaft having a proximal end and a distal end, at least one longitudinal cavity being formed in an outer surface of the elongate shaft and extending between the proximal and distal ends of the elongate shaft, wherein the at least one longitudinal cavity is configured for disposal of the at least one force transmitting member therein such that the at least one force transmitting member is translatable relative to the elongate shaft;
    an end effector supported on the elongate shaft, the end effector including:
        a wrist assembly pivotally connected to the distal end of the elongate shaft; and
        a jaw assembly connected to the wrist assembly, the jaw assembly including:
            a first pulley pivotally connected to the wrist assembly; and
            a second pulley pivotally connected to the wrist assembly, wherein the second pulley is spaced apart from the first pulley; and
    at least one force transmitting member including:
        a single first cable secured to at least one point along the first pulley, wherein the single first cable extends distally from the elongate shaft, wraps around at least a portion of the first pulley, and returns into the elongate shaft; and
        a single second cable secured to at least one point along the second pulley, wherein the single second cable extends distally from the elongate shaft, wraps around at least a portion of the second pulley, and returns into the elongate shaft.

2. The endoscopic surgical assembly as recited in claim 1, wherein the at least one longitudinal cavity has a key-hole shaped transverse cross-sectional profile and the elongate shaft is non-cannulated.

3. The endoscopic surgical assembly as recited in claim 1, wherein the at least one longitudinal cavity has a diameter substantially equal to a diameter of the at least one force transmitting member.

4. The endoscopic surgical assembly as recited in claim 1, further comprising a sleeve disposable about the elongate shaft to sheath the at least one force transmitting member within the at least one longitudinal cavity, and to retain the at least one force transmitting member between the outer surface of the elongate shaft and the sleeve.

5. The endoscopic surgical assembly as recited in claim 1, wherein the at least one longitudinal cavity includes a plurality of longitudinal cavities disposed in parallel alignment circumferentially about the elongate shaft.

6. The endoscopic surgical assembly as recited in claim 5, wherein a force transmitting member is slidably disposed within each longitudinal cavity.

7. The endoscopic surgical assembly as recited in claim 1, wherein the jaw assembly further comprises a third cam pulley pivotally connected to the wrist assembly, wherein the third cam pulley is interposed between the first pulley and the second pulley; and wherein the at least one force transmitting member includes a third cable at least partially wrapped around the third cam pulley and secured to at least one point along the third cam pulley.

* * * * *